United States Patent [19]

Tillinghast, III et al.

[11] Patent Number: 5,766,140
[45] Date of Patent: Jun. 16, 1998

[54] ANGULAR COMPENSATION DEVICE FOR A JOINT BRACE

[75] Inventors: Theodore V. Tillinghast, III, Carlsbad; Richard E. Gildersleeve, Escondido, both of Calif.

[73] Assignee: Smith & Nephew Donjoy, Inc., Carlsbad, Calif.

[21] Appl. No.: 640,489

[22] Filed: May 1, 1996

[51] Int. Cl.$^6$ ........................................ A61F 5/00
[52] U.S. Cl. .................. 602/16; 602/26; 403/87
[58] Field of Search .................... 602/5, 16, 20, 602/23, 24, 26; 601/23, 33, 34; 403/87, 85, 84, 83, 118

[56] References Cited

U.S. PATENT DOCUMENTS

| | | | |
|---|---|---|---|
| 25,085 | 9/1859 | Rooney et al. | 16/307 |
| 1,381,290 | 6/1921 | Diadul, Jr. . | |
| 3,030,135 | 4/1962 | Polanski | 403/87 |
| 3,902,482 | 9/1975 | Taylor | 602/26 X |
| 4,378,009 | 3/1983 | Rowley et al. . | |
| 4,732,143 | 3/1988 | Kausek et al. | 602/16 |
| 4,817,588 | 4/1989 | Bledsoe . | |
| 4,872,448 | 10/1989 | Johnson, Jr. . | |
| 4,881,299 | 11/1989 | Young et al. | 602/16 X |
| 4,881,532 | 11/1989 | Borig et al. | 602/16 |
| 4,938,207 | 7/1990 | Vargo . | |
| 4,940,044 | 7/1990 | Castillo | 602/16 |
| 4,955,369 | 9/1990 | Bledsoe et al. . | |
| 5,086,760 | 2/1992 | Neumann et al. . | |
| 5,100,403 | 3/1992 | Hotchkiss et al. | 602/16 X |
| 5,131,385 | 7/1992 | Kuehnegger et al. . | |
| 5,135,469 | 8/1992 | Castillo . | |
| 5,230,695 | 7/1993 | Silver et al. . | |
| 5,267,946 | 12/1993 | Singer et al. | 602/16 |
| 5,267,950 | 12/1993 | Weddendorf | 602/16 X |
| 5,277,698 | 1/1994 | Taylor . | |
| 5,286,250 | 2/1994 | Meyers et al. | 602/16 |
| 5,302,169 | 4/1994 | Taylor . | |
| 5,360,394 | 11/1994 | Christensen . | |
| 5,378,224 | 1/1995 | Billotti . | |
| 5,383,843 | 1/1995 | Watson et al. . | |
| 5,385,538 | 1/1995 | Mann . | |
| 5,400,806 | 3/1995 | Taylor . | |
| 5,407,421 | 4/1995 | Goldsmith . | |
| 5,415,625 | 5/1995 | Cassford et al. . | |
| 5,433,699 | 7/1995 | Smith, III . | |
| 5,437,615 | 8/1995 | Pekar et al. . | |
| 5,451,201 | 9/1995 | Prengler . | |
| 5,457,891 | 10/1995 | Taylor . | |
| 5,458,565 | 10/1995 | Tillinghast, III et al. . | |
| 5,462,517 | 10/1995 | Mann . | |

*Primary Examiner*—Linda C. Dvorak
*Attorney, Agent, or Firm*—Brown, Martin, Haller & McClain LLP

[57] ABSTRACT

An angular compensation hinge for a human joint brace, as well as the brace into which the hinge is incorporated, are described. The hinge's hinge pin and leaves cooperate with an arch bar through guide pins and a bi-threaded screw to provide angular compensation adjustment of the brace. The hinge can be easily operated by the user without assistance and by rotation of a single screw, either with a simple tool or through a knob, and provides for infinite angular adjustment over the entire adjustment range. Adjustments can be easily made while the user is wearing the brace. There is positive locking of the hinge at any angle within the range of adjustment. A few standard sizes of the brace will be sufficient to provide essentially customized fitting braces for virtually any person because of the "fine tuning" capability provided. The hinge may be used with many different types of braces, including those intended for knee, wrist, elbow, ankle, hip and shoulder joints. It is of particular utility with braces intended to relieve osteoarthritis pain, especially for those braces in which an adjustable condyle pad is used to provide the pain- and pressure-relieving force against the joint.

20 Claims, 2 Drawing Sheets

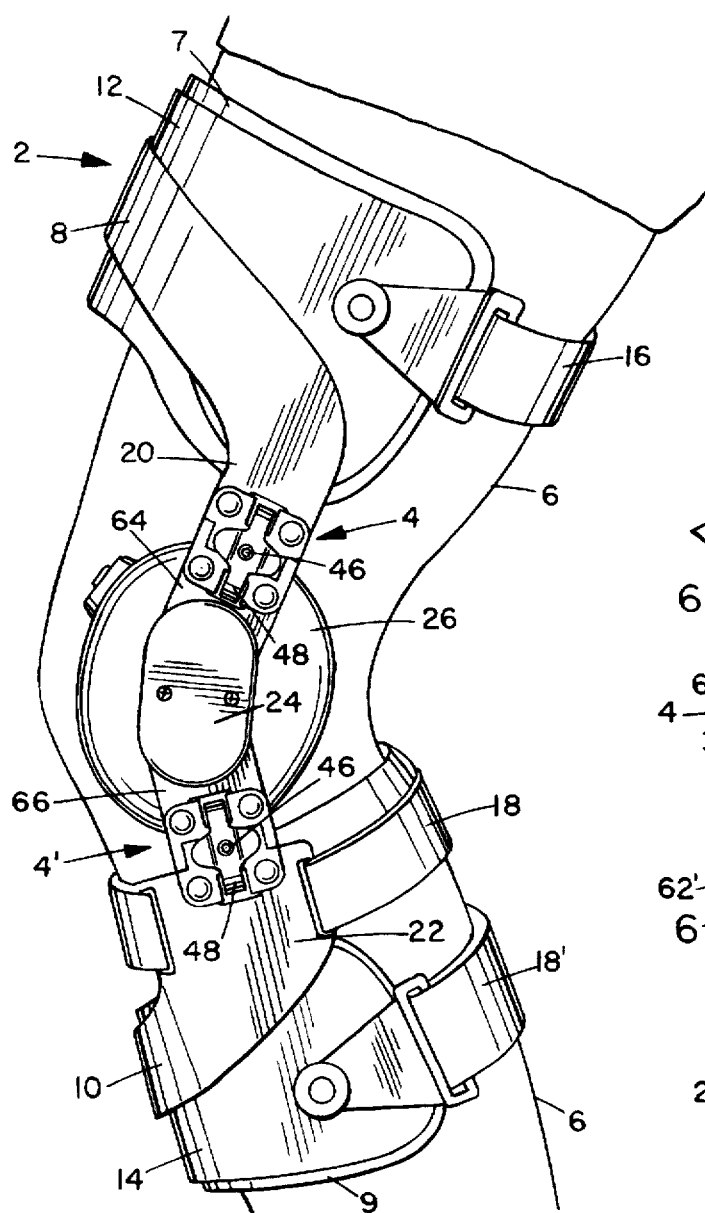
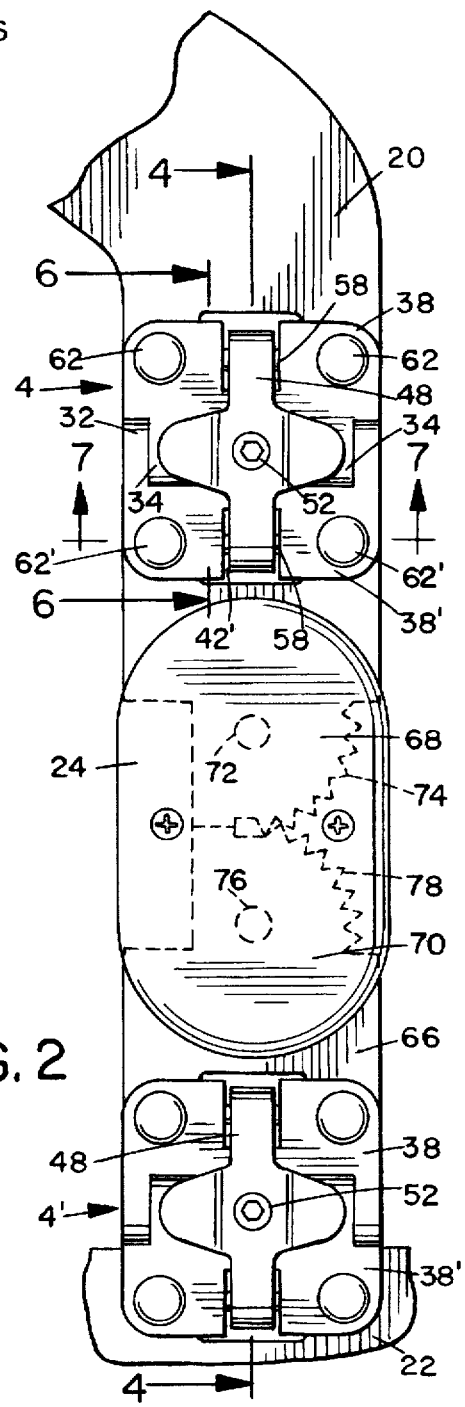
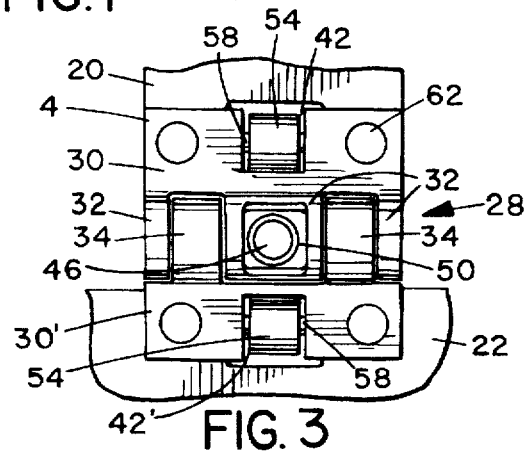
FIG. 1
FIG. 2
FIG. 3

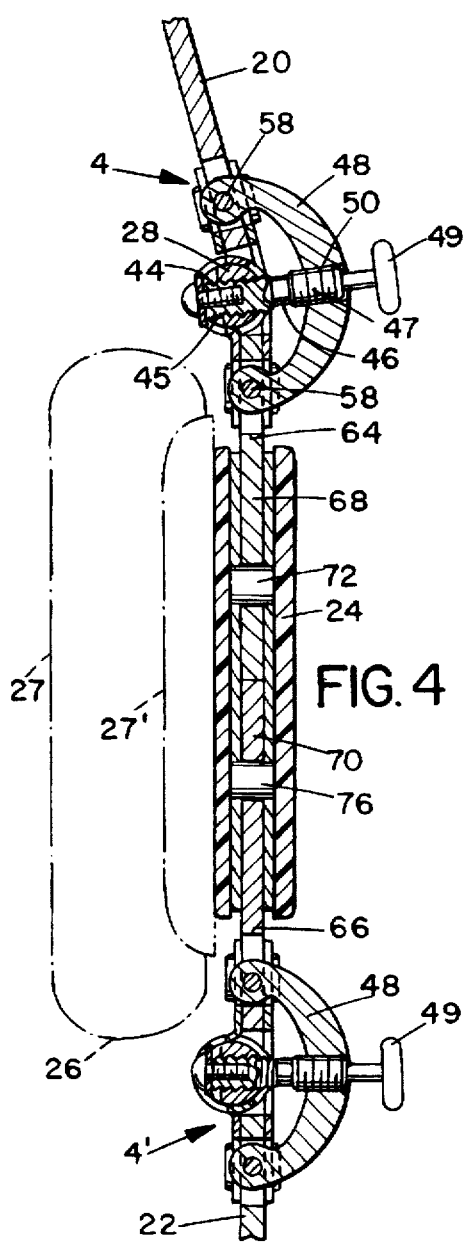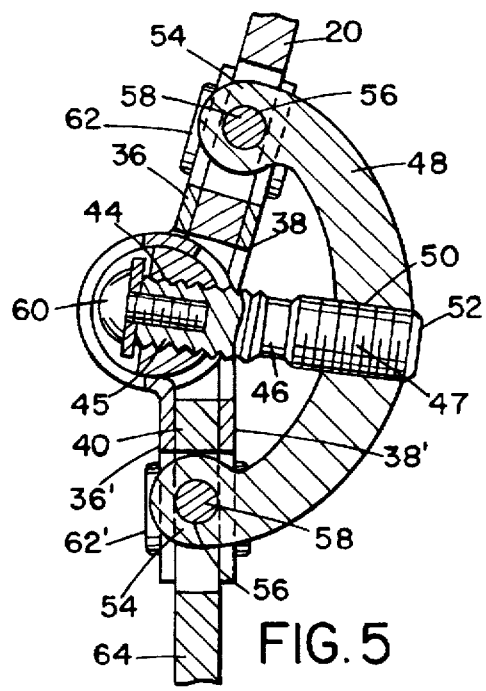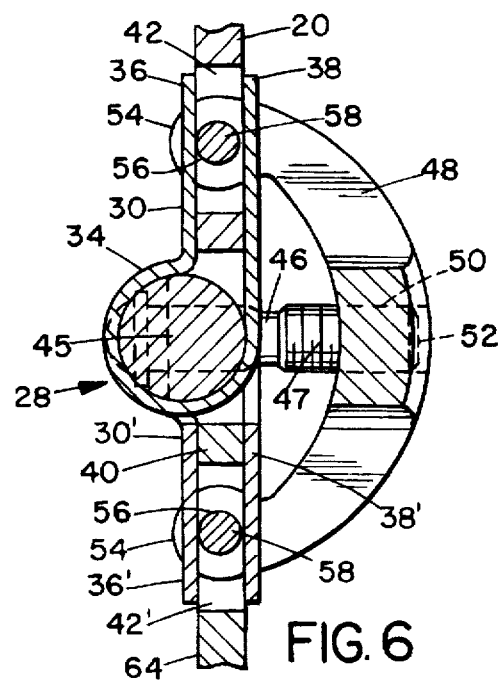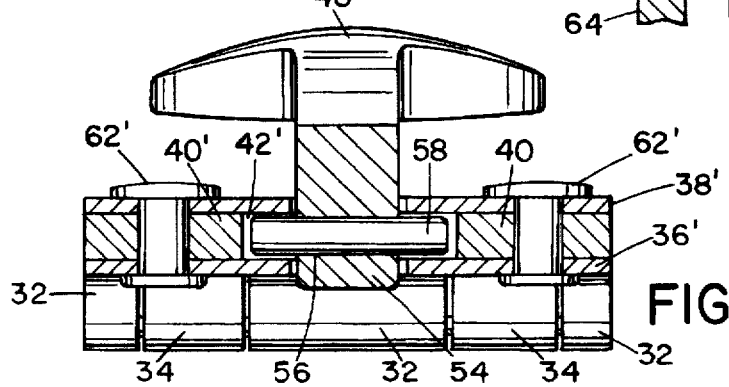

5,766,140

ANGULAR COMPENSATION DEVICE FOR A JOINT BRACE

BACKGROUND OF THE INVENTION

1. Field of the Invention

The invention herein relates to braces for human body joints, especially for joints such as the knee, elbow, hip, ankle, wrist and shoulder. More particularly it relates to joint brace structures intended to compensate for angular variations in human joints, including braces intended to provide relief from pain in such joints resulting from osteoarthritis.

2. Description of the Prior Art

Since there is substantial diversity in the shape and configuration of human joints, especially joints which have been diseased or damaged, designers and manufacturers of joint braces must find ways to accommodate such differences in order to produce and sell successful products. The two body portions connected through a joint have a "normal" alignment range which will be found in the large majority of people. However, some people will have alignments falling outside of the normal range. For instance, most people have a "normal" alignment of the legs through the knees, but some people have a laterally directed alignment ("bowlegged") or medially directed alignment ("knock-kneed"). For these latter people, joint brace structures designed for "normal" alignments often cannot provide optimum protective or therapeutic effect, and may be uncomfortable for the wearer. Proper fitting of braces to such people requires that a brace incorporate structure which can be conformed to a person's individual joint alignment.

In the past several different types of accommodation for individual joint alignment have been used. For instance, braces can be custom-made, to be conformed directly to and specifically for an individual patient. Such is appropriate in many cases, especially where the patient's condition is relatively unusual or the patient must function in unusually stressful environments (e.g., a football player). However, such custom-made braces are quite expensive and are not the best choice for many patients. Alternatively, a series of braces can be manufactured, in which each brace in the series has a different angular configuration. Manufacturing such a series is costly, and since there are definite incremental "steps" between the configurations of the sequential braces, accommodation of intermediate joint alignments remains a problem.

In an attempt to provide greater variability and accommodation, special hinges or joints have been incorporated into different types of braces. Considering a knee brace as an example, "varus/valgus" hinges may be positioned between the flexion hinge and either or both of the thigh or calf cuffs to allow the brace to be adjusted to accommodate the wearer's bowleggedness or knock-kneedness. By having a brace with such special accommodation hinges, the manufacturer can minimize the number of different brace sizes required for production or for customers' inventory.

However, In the past such accommodation or angular hinges, while generally accomplishing the desired end purpose, have suffered from significant deficiencies. Some of the hinges have had a gear-like structure, allowing positioning only at predetermined incremental intervals. Thus, it was not possible to "fine tune" the hinge for the optimum protective or therapeutic effect which might be required for a specific user. Further, many such hinges can be adjusted only by removing the brace entirely, to enable the wearer to have access to the adjustment mechanism of the hinge. Thus, during an extended wearing period, a wearer may find the brace becoming uncomfortable, and he or she wishes to make some adjustment in the hinge angle to maintain a desired level of wearing comfort. Such removal and adjustment, however, is often not only awkward but in some circumstances may be embarrassing or inappropriate. In addition, to obtain the optimum degree of adjustment of such hinges often requires several repetitions of removal, adjustment and replacement of the brace until the wearer is satisfied.

Some types of braces are intended for activities such as sports, to protect an otherwise healthy joint or a healed joint from damage or to provide support to the joint as the wearer engages in such activities. Other braces, however, are intended to be used for joint pain relief, particularly relief from osteoarthritic pain such as pain arising from medial or lateral compartment osteoarthritis in knee joints. Such braces function by exerting a force against the joint. Such pressure alters the contact between the opposed bone condyles so that pressure is decreased and the pain relieved.

Several prior art braces are relevant to the present invention. In U.S. Pat. Nos. 5,302,169 and 5,400,806 (both to Taylor) braces are disclosed which use an angular hinge structure in the brace to apply force to a joint. Screws are used to set the angle of each hinge and thus the force applied to the joint. In the hinges themselves, either a) one or two screws are merely loosened, the brace arm angle repositioned manually, and then the screws reset to hold the manually repositioned angle, or b) two screws must be loosened and then tightened independently and sequentially, with the first screw's loosening allowing the hinge angle to move a certain amount, the second screw's tightening then securing that position while the suitability of the force is determined by the wearer and the physician or therapist, then the sequence repeated until a suitable force is finally reached and secured.

A similar brace is illustrated in U.S. Pat. No. 5,131,385 (to Kuehnegger et al.), in which the angular hinge in the brace is also used to apply force to the joint. In the disclosed brace, the angular accommodation is on the anterior side of the brace, and consists of a pivoting tongue attached to the cuff and anterior extensions of the lateral and medial extension arms. Two screws fitted into oversize holes can be loosened to allow the tongue to pivot, thereby allowing the angle between the cuff and the central hinges to be varied. Neither the pivoting tongue nor the screws cause or regulate the change in the angle; they merely secure an angle which has been manually positioned. The cuff and/or central hinges must be moved to the desired new position after the screws are loosened and then the cuff and hinges must be held at that angle while the screws are tightened. Essentially this will take two people, since one person must loosen the screws, while the other first holds, then moves, and then retains the cuff and/or hinges at the desired angle while the first person then tightens the screws. Further, since the screws are seated in oversized holes, there is little restraint on them other than the frictional force of their being tightened against the surfaces of the arm extensions.

In contrast, in the braces disclosed in U.S. Pat. Nos. 5,415,625 (to Cassford et al.) and 5,458,565 (to Tillinghast et al.) adjustable condyle pads are incorporated into the brace and pneumatic adjustment of the condyle pad creates the force applied against the joint. The brace structure functions to position the condyle pad, and it is the adjustable condyle pad affixed to the side of the flexion hinge facing the joint that creates the force, with the brace maintaining the condyle pad in position.

SUMMARY OF THE INVENTION

The above-mentioned deficiencies of the prior art angular compensation hinges or joints and the braces they have been used in have now been overcome in the angular compensation hinge device of the present invention. The present hinge provides for infinite angular adjustment over the entire adjustment range by rotation of a single screw. Adjustments can be easily and discreetly made by the user without requiring assistance, and while the user is wearing the brace. The device provides for positive locking at any angle within the range of adjustment. Also, no special or cumbersome tools are needed to make the adjustment, since the hinge can be easily operated with a simple hex wrench, screwdriver or equivalent tool, or by a built-in knob.

The hinge can be used with both medially and laterally directed braces, and with both braces intended primarily for vigorous activities (e.g., sports) and those intended for medical or physiological applications (e.g., osteoarthritis braces). Because of the extensive adjustment capabilities of the present device, it is contemplated that a few standard sizes will be sufficient to provide essentially customized fitting braces for virtually any person, thus simplifying the production tooling and related requirements for manufacturers and the inventory requirements of vendors and medical personnel.

Generally, then, the invention involves an angular compensation hinge or joint which has a hinged portion with a hinge pin and two hinge leaves which can rotate relative to each other around the pin, an arch bar with guide pins in its ends positioned in recesses in the other ends of the leaves, and a bi-threaded screw operably connecting the hinge pin and the arch bar. When the screw is rotated, the arch bar and hinge pin move toward or away from each other, and the guide pins cause the hinge leaves to rotate relative to each other. In practice the angular compensation hinge may be incorporated into an osteoarthritic brace between a cuff and the flexion hinge, so that the movement of the hinge leaves will impart an angular adjustment to the brace. Usually there will be two angular compensation hinges in the brace, one on either side of the central hinge, so that angular adjustments can be made relative to either or both of the cuffs with respect to the flexion hinge. Other configurations are also possible; for instance, in braces which have a tripartite structure with two flexion hinges connected by a bar, the angular compensation hinge may be incorporated into that connecting bar. Preferably adjustment will be by a simple tool such as a screwdriver (straight blade, Phillips head, etc.), a hex wrench or an Allen wrench. Alternatively, the hinge may be operated by a built-in knob which can be easily turned by the wearer. Pneumatic adjustment of the condyle pad for application of force to the joint may be made as disclosed in the aforementioned Cassford et al. and Tillinghast et al. patents.

Therefore, in a first broad embodiment, the present invention is thus an angular compensation device for a human joint brace, the brace comprising a pair of securing members for securement of the brace adjacent to the joint, the device comprising an angular compensation hinge disposed between the securing members, the angular compensation hinge comprising a hinge pin and a pair of leaves pivotable thereon; a bar moveably attached at its ends to the leaves; and a screw threadedly engaged with the hinge pin and the bar; such that rotation of the screw causes the hinge leaves to pivot on the hinge pin, thereby causing angular adjustment between the securing members.

In a narrower embodiment, in the angular compensation device the angular compensation hinge comprises a hinge pin and a pair of oppositely extending hinge leaves pivoting on the hinge pin, each hinge leaf having a recess formed therein, and the hinge pin having a central threaded hole therein; the bar comprises an elongated arch bar; the screw comprises a bi-directional threaded screw; the elongation arch bar being connected to the hinge pin by the bi-threaded screw and having a hole extending though each of the ends thereof, each end extending into the recess in a proximal leaf, a guide pin seated in each hole with ends thereof extending into the recess and moveable therein, and a central threaded hole, the threading of the hole being opposite in pitch from threading of the central threaded opening in the hinge pin; and the bi-threaded screw being threadedly engaging at its opposite ends in the arch bar hole and the hinge pin hole, the screw having means for rotation thereof operable while the brace is being worn by a user; such that rotation of the screw causes the arch bar and the hinge pin to be displaced relative to each other and the guide pins to move within the recesses, causing the hinge leaves to rotate relative to each other, the hinge leaf movement in cooperation with the arch bar and captured guide pins in the recesses causing angular adjustment of the brace.

Also disclosed is an osteoarthritic brace comprising a pair of securing members comprising means for attachment of the brace adjacent to the joint; a flexion hinge disposed between and cooperative with the securing members; an angular compensation device of the type described above disposed between and cooperative with the securing members; and an adjustable condyle pad fixed to a side of the flexion hinge facing the joint and in contact with the joint, adjustment of the condyle pad causing a force to be exerted against the joint, the force altering contact and pressure between opposed bone condyles in the joint and thereby relieving osteoarthritic pain caused by such contact and pressure.

In another broad embodiment, the invention herein is a brace for a body joint and having angular compensation capability, which comprises a pair of securing members comprising means for attachment of the brace, each securing member having an extension portion extending toward the joint; a flexion hinge aligned with the joint and disposed between and connecting opposed ends of the extension portions; and an angular compensation device incorporated into one of the extensions, the device comprising: an angular compensation hinge disposed between and connected to the flexion hinge and one of the securing members, the angular compensation hinge comprising a hinge pin and a pair of leaves pivotable thereon; a bar moveably attached at its ends to the leaves; and a screw threadedly engaged with the hinge pin and the bar; such that rotation of the screw causes the hinge leaves to pivot on the hinge pin, thereby changing the angle defined by the angular compensation hinge and causing angular adjustment of the brace.

In another broad embodiment, the invention herein is an osteoarthritic brace for relieving osteoarthritic pain in a body joint and having angular compensation capability, which comprises a pair of securing members comprising means for attachment of the brace, each securing member having an extension portion extending toward the joint; a flexion hinge aligned with the joint and disposed between and connecting opposed ends of the extension portions; and an angular compensation device incorporated into one of the extensions, the device comprising an angular compensation hinge disposed between and connected to the flexion hinge and one of the securing members, the angular compensation hinge comprising a hinge pin and a pair of leaves pivotable thereon; a bar moveably attached at its ends to the leaves;

and a screw threadedly engaged with the hinge pin and the bar; such that rotation of the screw causes the hinge leaves to pivot on the hinge pin, thereby changing the angle defined by the angular compensation hinge and causing angular adjustment of the brace; and an adjustable condyle pad fixed to a side of the flexion hinge facing the joint and in contact with the joint, adjustment of the condyle pad causing a force to be exerted against the joint, the force altering contact and pressure between opposed bone condyles in the joint and thereby relieving osteoarthritic pain caused by such contact and pressure.

In such braces the flexion hinge and the angular compensation hinge normally provide angular movement in different planes.

Sets of such braces, comprising a few separate sizes of brace, are also included.

BRIEF DESCRIPTION OF THE DRAWINGS

FIG. 1 is a pictorial view showing a knee brace mounted on a wearer's leg and incorporating the novel varus/valgus hinge of this invention.

FIG. 2 is an enlarged side view of the hinge in straightened position.

FIG. 3 is a rear view of the hinge at the lower end of FIG. 2.

FIG. 4 is a sectional view taken on line 4—4 of FIG. 2.

FIG. 5 is an enlargement of the upper hinge of FIG. 4, with the hinge inclined in the opposite direction.

FIG. 6 is an enlarged sectional view taken on line 6—6 of FIG. 2.

FIG. 7 is an enlarged sectional view taken on line 7—7 on FIG. 2.

DETAILED DESCRIPTION AND PREFERRED EMBODIMENTS

For brevity herein the joint of application for the invention will be exemplified by the knee, and the angular compensation as varus/valgus compensation of the leg and knee. It will be understood, however, that the invention described and claimed herein is equally applicable to many body joints generally, including, but not limited to, the knee, elbow, wrist, ankle, hip and shoulder. Consequently the description which follows should not be considered as limited only to knee braces.

The invention herein is best understood by reference to the drawings. The view in FIG. 1 is of a knee brace 2, here exemplified by an osteoarthritis brace, mounted on a wearer's leg 6. The view represents, alternatively, such a brace mounted on the lateral side of the wearer's left leg to provide medially directed force against the left knee joint, or, such a brace mounted on the medial side of the wearer's right leg to provide laterally directed force against the right knee joint. A mirror image brace will be used in the opposite applications. It will therefore be evident that braces, and the varus/valgus hinge device of the present invention which they incorporate, can be designed for either side of the leg. For braces such as osteoarthritis braces, where force is to be exerted against the knee, the force can be exerted either laterally or medially, depending on the design of the brace.

While the varus/valgus hinge invention herein will for brevity be discussed and illustrated with an osteoarthritis brace, it will be understood that the hinge is applicable to all types of joint braces, including both those intended to be worn for support and protection during strenuous activities and those intended to be worn to alleviate or control a medical or physiological condition.

As noted, in FIG. 1 an osteoarthritis knee brace, generally designated 2, and incorporating a pair of varus/valgus hinges 4 and 4' of the present invention, is shown as being secured to the leg 6 of a wearer. (For the purpose of discussion and example herein, it will be assumed that FIG. 1 illustrates the lateral side of the wearer's left leg, and that the force of the brace 2 is being exerted medially. This discussion will of course be equally applicable to all other configurations.) The brace 2 consists of generally semicircular thigh cuff 8 and calf cuff 10, both made of substantially rigid but slightly flexible material such as plastic or metal. Each cuff 8 and 10 has attached to its interior a flexible plastic shell indicated respectively at 12 and 14, which in turn has a lining of foam padding, indicated respectively as 7 and 9, for comfort, and is secured by straps 16, 18 and 18', respectively. The semicircular cuffs 8 and 10 are bent at the lateral end thereof to continue in the form of extension arms 20 and 22, respectively, disposed on the lateral side of the leg 6. The extension arms 20 and 22 are normally disposed generally at an angle of about 70°–90° from the normal generally horizontal orientation of each cuff (when the wearer is standing upright), such that the extensions run parallel to the user's leg and extend generally vertically toward each other. If there were no varus/valgus hinges 4, the extensions 20 and 22 would each be connected to the central flexion/extension hinge 24. Details of central hinge 24 will be illustrated and discussed below. Disposed on the medial side of the hinge 24 and secured thereto is a condyle pad 26, the outer side 27 of which is in contact with the lateral side of the wearer's knee. If will be understood that the force to be exerted against the knee in an osteoarthritis brace is developed by adjustment of the condyle pad 26, with the brace structure retaining the condyle pad 26 in place, as indicated in the aforesaid Tillinghast et al and Cassford et al. patents. The combination of that brace with adjustable condyle pad and the present angular compensation hinge provides an unique and exceptional brace. However, the angular compensation device of this invention is not limited to use only with braces having adjustable condyle pads.

FIGS. 2 and 3 illustrate key aspects of the structure of the varus/valgus hinges 4 and 4' and their cooperation with the other components of the brace 2. (In most of the Figures, two varus/valgus hinges 4 and 4' are illustrated. That is the usual and most preferable configuration, making adjustments possible on both the thigh and calf side of the hinge 24. However, since the varus/valgus hinges 4 and 4' are identical, only one need be described as exemplary. For brevity herein, only upper hinge 4 connected to the thigh cuff will be described. It will be recognized, of course, that the lower hinge 4' operates in an identical manner with respect to the calf cuff 10.) The central member of the hinge 4 is a hinge pin 28 which extends across the width of the hinge 4. Mounted on hinge pin 28 and rotatable in relation thereto, in normal hinging motion, are hinge leaves 30 and 30'. It will be recognized that these hinge leaves 30 and 30' are substantially identical except for the structure of their attachment mounting on the hinge pin 28. In the manner conventional for hinges, one of the hinge leaves (in this case hinge leaf 30) is mounted with three curved arms 32 which are sufficiently spaced apart to allow the two curved arms 34 of leaf 30' to be mounted on hinge pin 28 between the arms 32. The hinge leaves 30 and 30' are formed with upper and lower members 36/38 and 36'/38' respectively joined by lateral braces 40/40', as best illustrated in FIGS. 5–7. A clear space 42/42' is left at each end of the hinge to accommodate a guide pin to be described below.

A threaded hole 44 extends through hinge pin 28 at its axial midpoint, as best illustrated in FIG. 5. Hole 44 has threaded into it one end 45 of a bi-directional right hand/left hand headless screw 46.

An arch bar 48 is also a part of the hinge 4 and has a central threaded hole 50, into which the opposite end 47 of the bi-threaded headless screw 46 extends. Holes 44 and 50 of course have opposite hand threading to correspond to the opposite hand threading of the respective ends of the bi-directional screw 46. It is from the end 47 of the screw 46 that the screw is rotated for adjustment of the hinge. In one alternative method (shown in FIG. 2) rotation is obtained by having in the end 47 of screw 46 a screwdriver-accepting slot (either a straight slot or a Phillips or other patterned slot), a hex socket or a similar tool-accommodating recess 52 to accommodate a separate adjusting tool (not shown), commonly a screwdriver, hex wrench or Allen wrench, or the equivalent. In another embodiment, the end 47 of the screw 46 is extended (as shown in FIG. 4) and a knob 49, knob-like bolthead or similar gripping device is attached thereto or formed thereon. The wearer can then grip this knob 49 and rotate the screw, without resort to use of any tools. The arch bar 48 extends parallel to the axis of the user's leg 6. At its outer ends, arch bar 48 is configured with a rounded knuckle 54 which contains a central lateral hole 56 extending therethrough, in which is mounted a guide pin 58. The outwardly extending ends of the guide pins 58 extend into the recess 42/42' between the upper and lower plates 36/38 and 36'/38', respectively, and are seated slightly loosely therein so that each can move within the recess as the hinge 4 is adjusted.

The end 45 of headless screw 46 extending through the hinge pin 28 is capped with a cap screw 60 threaded into the tip of end 45 (as illustrated in FIG. 5) to provide a limit for the travel of screw 46 and therefore for the movement of hinge 4. The range of movement permitted to the hinge 4 will depend upon the lengths of the oppositely threaded ends 45 and 47 of headless screw 46.

The hinge 4 is secured at its upper end to extension arm 20 of cuff 10 by rivets 62 and at its lower end to a short extension member 64, which extends outwardly from central hinge 24, by rivets 62'. Member 64 is integrally formed with the upper rotatable gear segment 68 of hinge 24. As the wearer's knee flexes or extends, segment 68 rotates on pivot pin 72 to mesh through teeth 74 with opposed gear segment 70, similarly pivoting on pivot pin 76 and engaging teeth 74 with teeth 78. On the opposite side of central hinge 24 there is an extension member 66, similar to extension member 64 but extending from segment 70. Calf varus/valgus hinge 4' is attached to that member 66 and bridges between member 66 and extension arm 22 of calf cuff 10, operating in the same manner as hinge 4.

From this description of its structure, the operation of the varus/valgus hinge 4 of the present invention can be readily understood from the Figures. As noted above, it has been assumed that FIG. 1 illustrates the lateral side of the wearer's left leg. When an operating tool is inserted into recess 52 and turned, or when the knob 49 is turned, the rotating motion of headless screw 46 will cause hinge pin 28 and its attached leaves 30 and 30' to rotate relative to the central segment of arch bar 48. Assuming that the end 47 of screw 46 has a right hand thread, when screw 46 is turned clockwise (as viewed in FIGS. 1 and 2) the motion of the screw 46 will be into the hole 50, forcing the hinge pin 28 away from the center of arch bar 48 and causing the extension 20 to rotate clockwise and member 64 to rotate counterclockwise relative to hinge pin 28, as illustrated in FIG. 5, with the guide pins 58 traversing the slots 42/42'. This movement will accommodate a person who is knock-kneed. Conversely, if the screw 46 is turned to traverse outwardly through arch bar 48 (counterclockwise in FIGS. 1 and 2), the hinge pin 28 will be drawn toward the arch bar 48, extension 20 will rotate counterclockwise and member 64 will move clockwise relative to hinge pin 28, as illustrated in FIG. 4, thus accommodating a person who is bowlegged.

The fit of the screw 46 in the holes 44 and 50 will be a moderately firm interference fit. The screw 46 must not be seated so tightly that the user cannot fairly easily turn it with a screwdriver or hex wrench, but conversely must be sufficiently tight so that when the rotation by the user is completed, the screw 46 will remain essentially "locked" in the position at which it was left, thus preventing further varus/valgus motion of the hinge 4 until the user elects to make a subsequent adjustment.

It will be evident that adjustment of this hinge can be made simply and unobtrusively. Thus, the user can readily adjust the device while sitting or standing and while in a variety of different business or social situations, without embarrassment and without calling undue attention to the activity.

It will also be evident that because of the ability of the screw 46 to be locked at any of an infinite number of positions throughout its range of motion, very fine tuning of the adjustment can be made in a single movement, which can be accomplished while the wearer continues to wear the brace. As the tool is manipulated, the wearer can sense when the most comfortable position has been reached, such that repeated iterations (as with the prior art hinges) to reach a comfortable position are not needed.

As noted, the angular compensation hinges and braces described herein are useful not only with knee joints but also with other body joints. Those skilled in the art will be aware that there will be minor configuration and size variations for different joints, but such are known and will be readily apparent. In any case, such variations do not materially affect or change the nature of the present invention related to the angular compensation device and its incorporation into different braces.

It will also be evident that there are numerous embodiments of this invention which, while not expressly described above, are clearly within the scope and spirit of the invention. The description above is therefore intended to be exemplary only, and the scope of the invention is to be limited solely by the appended claims.

We claim:

1. An angular compensation device comprising:
   an angular compensation hinge comprising a hinge pin and a pair of leaves pivotable thereon;
   a bar moveably attached at its ends to said leaves; and
   a rotatable screw threadedly engaged with said hinge pin and said bar,
   rotation of said screw causing said hinge leaves to pivot on said hinge pin;
   such that when said pair of leaves are attached respectively to adjacent halves of a human joint brace, rotation of said screw and pivoting of said leaves causes angular adjustment between said halves respective to each other.

2. A device as in claim 1 comprising an angular compensation hinge having one leaf of said pair of leaves attached to and cooperative with a flexion hinge such that when said one leaf is attached to one half of a human joint brace through said flexion hinge and an other leaf of said pair of leaves is attached to another half of said brace, rotation of said screw and pivoting of said leaves causes angular adjustment between said halves respective to each other.

3. A device as in claim 1 wherein said screw is rotatable by a tool or directly by manipulation.

4. A device as in claim 1 wherein:

said angular compensation hinge comprises a hinge pin and a pair of oppositely extending hinge leaves pivoting on said hinge pin, each said hinge leaf having a recess formed therein, and said hinge pin having a central threaded hole therein;

said bar comprises an elongated arch bar;

said screw comprises a bi-directional threaded screw;

said elongated arch bar being connected to said hinge pin by said bi-threaded screw and having a hole extending though each of the ends thereof, each end extending into said recess in a proximal leaf, a guide pin seated in each said hole with ends thereof extending into said recess and moveable therein, and a central threaded hole, the threading of said hole being opposite in pitch from threading of said central threaded opening in said hinge pin; and said bi-threaded screw being threadedly engaging at its opposite ends in said arch bar hole and said hinge pin hole, said screw having means for rotation thereof operable by a user of said device while said device is in use;

rotation of said screw causing said arch bar and said hinge pin to be displaced relative to each other and said guide pins to move within said recesses, causing said hinge leaves to rotate relative to each other.

5. A device as in claim 4 wherein said leaves comprise means for attachment of said device to a human joint brace.

6. A device as in claim 2 wherein said screw incorporates means for rotation at one end of said screw which comprises a tool engaging slot or a shaped recess, said slot or recess cooperating with a separate rotation-causing tool, or a manually grippable and rotatable knob.

7. An osteoarthritic brace comprising:

a pair of securing members comprising means for attachment of said brace adjacent to a human joint;

a flexion hinge disposed between and cooperative with said securing members;

an angular compensation device disposed between and cooperative with said securing members, said angular compensation device comprising an angular compensation hinge comprising a hinge pin and a pair of leaves pivotable thereon;

a bar moveably attached at its ends to said leaves; and a rotatable screw threadedly engaged with said hinge pin and said bar, rotation of said screw causing said hinge leaves to pivot on said hinge pin; and an adjustable condyle pad fixed to a side of said flexion hinge adapted to face said joint and to be in contact with said joint;

such that adjustment of said condyle pad applies a force against said joint, said force altering contact and pressure between opposed bone condyles in said joint and thereby relieving osteoarthritic pain caused by such contact and pressure.

8. A brace for a body joint and having angular compensation capability, which comprises:

a pair of securing members comprising means for attachment of said brace, each securing member having an extension portion adapted to extend toward said joint when said brace is in use;

a flexion hinge disposed between and connecting opposed ends of said extension portions; and an angular compensation device incorporated into one of said extensions, said device comprising:

an angular compensation hinge disposed between and connected to said flexion hinge and one of said securing members, said angular compensation hinge comprising a hinge pin and a pair of leaves pivotable thereon;

a bar moveably attached at its ends to said leaves; and a screw threadedly engaged with said hinge pin and said bar;

such that rotation of said screw causes said hinge leaves to pivot on said hinge pin, thereby changing the angle defined by said angular compensation hinge and causing angular adjustment of said brace.

9. A brace as in claim 8 comprising a pair of said angular compensation devices, disposed respectively on either side of said flexion hinge.

10. A brace as in claim 8 wherein said extensions and flexion hinge are disposed on the medial side of said brace when said brace is in use.

11. A brace as in claim 8 wherein said extensions and flexion hinge are disposed on the lateral side of said brace when said brace is in use.

12. A brace as in claim 8 wherein said flexion hinge and said angular compensation hinge provide angular movement in different planes.

13. A set of braces comprising a plurality of braces, at least one of said braces being of a different overall size from at least one other brace of said plurality, and each brace of said plurality comprising:

a pair of securing members comprising means for attachment of said brace, each securing member having an extension portion adapted to extend toward said joint when said brace is in use;

a flexion hinge disposed between and connecting opposed ends of said extension portions; and an angular compensation device incorporated into one of said extensions, said device comprising:

an angular compensation hinge disposed between and connected to said flexion hinge and one of said securing members, said angular compensation hinge comprising a hinge pin and a pair of leaves pivotable thereon;

a bar moveably attached at its ends to said leaves; and a screw threadedly engaged with said hinge pin and said bar;

such that rotation of said screw causes said hinge leaves to pivot on said hinge pin, thereby changing the angle defined by said angular compensation hinge and causing angular adjustment of said brace.

14. An osteoarthritic brace for relieving osteoarthritic pain in a body joint and having angular compensation capability, which comprises:

a pair of securing members comprising means for attachment of said brace, each securing member having an extension portion adapted to extend toward said joint when said brace is in use;

a flexion hinge disposed between and connecting opposed ends of said extension portions; and an angular compensation device incorporated into one of said extensions, said device comprising:

an angular compensation hinge disposed between and connected to said flexion hinge and one of said securing members, said angular compensation hinge comprising a hinge pin and a pair of leaves pivotable thereon;

a bar moveably attached at its ends to said leaves; and a screw threadedly engaged with said hinge pin and said bar;

such that rotation of said screw causes said hinge leaves to pivot on said hinge pin, thereby changing the angle defined by said angular compensation hinge and causing angular adjustment of said brace; and an adjustable condyle pad fixed to a side of said flexion hinge facing said joint and in contact with said joint;

such that adjustment of said condyle pad applies a force against said joint, said force altering contact and pressure between opposed bone condyles in said joint and thereby relieving osteoarthritic pain caused by such contact and pressure.

15. A brace as in claim 14 comprising a pair of said angular compensation devices, disposed respectively on either side of said flexion hinge.

16. A brace as in claim 14 wherein said extensions, flexion hinge and condyle pad are disposed on the medial side of said brace when said brace is in use.

17. A brace as in claim 14 wherein said extensions, flexion hinge and condyle pad are disposed on the lateral side of said brace when said brace is in use.

18. A brace as in claim 14 wherein said condyle pad is pneumatically inflatable and deflatable.

19. A brace as in claim 14 wherein said flexion hinge and said angular compensation hinge provide angular movement in different planes.

20. A set of osteoarthritic braces comprising a plurality of braces, at least one of said braces being of a different overall size from at least one other brace of said plurality, and each of said braces comprising a pair of securing members comprising means for attachment of said brace, each securing member having an extension portion adapted to extend toward said joint when said brace is in use;

a flexion hinge disposed between and connecting opposed ends of said extension portions; and an angular compensation device incorporated into one of said extensions, said device comprising:

an angular compensation hinge disposed between and connected to said flexion hinge and one of said securing members, said angular compensation hinge comprising a hinge pin and a pair of leaves pivotable thereon;

a bar moveably attached at its ends to said leaves; and a screw threadedly engaged with said hinge pin and said bar;

such that rotation of said screw causes said hinge leaves to pivot on said hinge pin, thereby changing the angle defined by said angular compensation hinge and causing angular adjustment of said brace; and an adjustable condyle pad fixed to a side of said flexion hinge facing said joint and in contact with said joint;

such that adjustment of said condyle pad applies a force against said joint, said force altering contact and pressure between opposed bone condyles in said joint and thereby relieving osteoarthritic pain caused by such contact and pressure.

* * * * *